United States Patent [19]

Stephan

[11] 4,082,734

[45] Apr. 4, 1978

[54] PRODUCTION OF INTRAVENOUSLY APPLICABLE NATIVE HUMAN IMMUNE GLOBULIN HAVING A NORMAL HALF-LIFE

[75] Inventor: Wolfgang Stephan, Dreieichenhain, Germany

[73] Assignee: Biotest-Serum-Institut GmbH, Frankfurt am Main-Niederrad, Germany

[21] Appl. No.: 687,842

[22] Filed: May 19, 1976

[30] Foreign Application Priority Data

Jun. 18, 1975 Germany ............................ 2527064

[51] Int. Cl.² ............................................. A23J 1/06
[52] U.S. Cl. ................................................. 260/112 B
[58] Field of Search ..................................... 260/112 B

[56] References Cited

U.S. PATENT DOCUMENTS

| 3,763,135 | 10/1973 | Shanbrom et al. | 260/112 B |
| 3,916,026 | 10/1975 | Stephan | 424/177 |
| 3,984,539 | 10/1976 | Khouw et al. | 260/112 B |

FOREIGN PATENT DOCUMENTS

| 2,018,394 | 7/1970 | France. |
| 1,198,277 | 7/1970 | United Kingdom. |

OTHER PUBLICATIONS

Concordance Sec., Chemical Abstracts, vol. 83, (1975), pp. 228dc.
Stephan, Chemical Abstracts, vol. 71:47,731v, (1969).

*Primary Examiner*—Walter C. Danison
*Attorney, Agent, or Firm*—Burgess, Dinklage & Sprung

[57] ABSTRACT

An intravenously applicable native human immune globulin of normal half-life, unchanged antibody activity and free from anti-complement activity, is produced by heating human plasma or serum for about ½ to 4 hours at about 50° to 60° C, followed by conventional fractionation.

5 Claims, No Drawings

PRODUCTION OF INTRAVENOUSLY APPLICABLE NATIVE HUMAN IMMUNE GLOBULIN HAVING A NORMAL HALF-LIFE

BACKGROUND

The invention relates to a gamma globulin suitable for intravenous administration, which can be obtained from human plasma without modifying processes.

It is known that a gamma globulin can be prepared by fractionation, which has the property of fixing complement non-specifically (Barandun, S., "Die Gamma Globulin-Therapie," S. Karger-Verlag, Basel 1963). This anticomplement activity is related to the formation of aggregates. Non-specific complement fixing gamma globulin is not suitable for intravenous administration, but only for intramuscular use. Since, however, the antibody activity is more complete in intravenous administration, and particularly since it starts immediately, attempts have been made to produce gamma globulin preparations that can be administered intravenously.

It is known that the biological function of antibodies is the elimination of bacteria and viruses and the neutralization of toxins. The antigen-binding part ($F_{ab}$) of the antibody molecule provides first for the recognition and neutralization of pathogens. The antigen-antibody complex that forms then activates the complement fixing part ($F_c$) of the molecule. A series of immunological reactions is thereby initiated, the most important of which are phagocytosis and the specific activation of the complement system. The specific activation of the complement system, which must be clearly distinguished from the non-specific (the anti-complement effect), produces bacteriolysis in the case of bacterial infections. As a further consequence of complement activation, anaphylatoxins and chemotactic factors are "metered" out. The anaphylatoxins, by increasing tissue permeability, provide for an increased antibody concentration at the site of the infection, while the chemotactic factors support phagocytosis. Thus, in the defense against infection, the $F_c$ part of the immunoglobulin-G molecule is of far-reaching importance. Of especial importance clinically is the in vivo half-life of the antibodies contained in intravenous gamma globulin. The longer the in vivo half-life, the longer the antibodies will circulate in the blood and the longer they will be available for prophylactic activity. This is of decisive importance in the case of diseases in whose course the organism is not capable of forming antibodies. In such cases it is necessary to administer the antibodies continually. The less often this is the case, the easier it will be to provide ambulatory treatment, especially.

Methods are already known for the production of an intravenously tolerable preparation from a standard gamma globulin (human) providing non-specific complement fixation. These methods are based on cleaving hydrolytically or enzymatically into its individual fragments the non-specific complement fixing standard globulin (human) obtained by conventional fractionating methods, such as Cohn's alcohol fractionation or Rivanol ammonium sulfate fractionation, and thus eliminating the non-specific complement-fixation or eliminating the anticomplement activity by chemical modification with beta-propiolactone. Specifically, these methods are the following:

Pepsin Decomposition (Schultze, H. E., and Schwick, C.: Dtsch. med. Wochenschrift, 87, 1643 (1962)).

Decomposition (Barandun, S. et al.: Vox Sang. 28, 157 (1975)).

HCl Treatment (Barandun, S. et al.: Vox Sang. 7, 187 (1962)).

Beta-Propiolactone Treatment (Stephan, W.: Z. klin. Chem. klin. Biochemie 7, 282 (1969)).

With regard to the half-life, the half-life of all known preparations is less than the natural half-life of 18 to 22 days. This is due to the drastic modification of the molecule by the enzymatic decomposition: antibody fragments are formed which have a high elimination rate. Controlled chemical modification by betapropiolactone delivers a decidedly better product having a half-life of 15 days. This, however, does not always achieve the object of the invention, namely, the isolation and concentration of human immune globulins having a natural, unaltered half-life of 18 to 22 days, free of anti-complement activity and therefore suitable for intravenous administration.

THE INVENTION

It has been found surprisingly that an intravenous immune globulin of natural half-life, free of anti-complement activity can be prepared from human plasma or serum.

The subject matter of the invention is an intravenous, native immune globulin (human) of natural half-life and unaltered antibody activity. This product is especially free of anti-complement activity. It cannot be distinguished from native immune globulin G in the serum and plasma by immune electrophoresis, by gel filtration or by ultracentrifugation.

The invention also extends to a method of preparing intravenous native immune globulin (human) of natural half-life and of the same antibody activity as the starting material, from human plasma or human serum, by heating the starting material for about ½ to 4 hours at about 50° to 60° C, preferably for about 2 hours at about 56° C, followed by fractionation in known manner, e.g. according to P. Kistler et al, Vox Sang. Vol. 7 (1962) page 414 and J. Hrejsi et al, Acta med. Scand. Vol. 155 (1956) page 65, the disclosures of which are incorporated herein by reference.

The invention is described in the following illustrative examples:

EXAMPLE 1

(a) One liter of citrate plasma (human from a pool of 1000 donors) was heated for 2 hours at 56° C. Then it was allowed to cool, and then, by the conventional Cohn alcohol fractionating process (Kistler, P. et al Vox Sang 7, 414 (1962)) the gamma globulin fraction was separated and a 5% solution in physiological saline solution was prepared.

(b) The process of (a) was repeated except that the fractionation was Rivanol ammonium sulfate fractionation (Hrejsi, J. et al, Acta med. Scand. 155, 65 (1956)).

EXAMPLE 2

Instead of citrate plasma, serum was used as starting material as well as ACD plasma containing a dextrose-containing citrate stabilizer, and was processed as in Example 1 (a) and (b).

EXAMPLE 3

Series tests were performed, in which the heating time was varied between ½ hour and 4 hours, and the temperatures were varied between 50° and 60° C, using the starting materials of Examples 1 and 2. It was found that, for small laboratory batches of less than one liter, short heating times at low temperatures were best, and for batches on a technical scale, i.e., of about 10 to 1000 liters, a longer heating time at higher temperature was best, for reasons of thermal equalization with regard to volume.

The advantageous properties of the product of the invention have been documented by the research described below, which was performed with a 5% solution.

1. CLINICAL TOLERABILITY

12 Adults and 24 children were each treated with a single dose of 0.1 to 0.5 ml per kilogram of the solution of Example 1(a). Of these, two patients had an antibody deficiency of the Bruton type; such patients are known to be especially sensitive to intravenous gamma globulin. The preparation was tolerated without reaction in all cases.

2. ANTI-COMPLEMENT ACTIVITY

The anti-complement titer is not greater than 1:5 in comparison with the sodium chloride control in the Kabat and Mayer hemolysis test, and is largely the same as that of commercially available intravenous immune globulin of various manufacture.

The following is extracted from the log of a complement determination:

3. ANTIBODY ACTIVITY

|  | Rubella | Rubeola |
|---|---|---|
|  | (Reciprocal titer in the hemoagglutination test) | |
| Plasma | 64 | 32 |
| Immune globulin of the invention | 512 | 128 |

Concentration factor approximately 4 to 8 (as determined mathematically).

4. HALF-LIFE

The half-life was determined by the double marking method with $^{125}$I and $^{131}$I in a comparison with intramuscular standard immune globulin (McFarlane, A. S.: Nature, London 182, 53 (1958)). A half-life of 20 days was found (natural half-life 18 to 22 days).

It will be appreciated that the instant specification and examples are set forth by way of illustration and not limitation, and that various modifications and changes may be made without departing from the spirit and scope of the present invention.

What is claimed is:

1. A method of preparing an intravenously applicable native-human immune globulin of substantially unchanged half-life and antibody activity but free from anti-complement activity, comprising heating human plasma or human serum for about 2 to 4 hours at about 50° to 56° C, and then fractionating, the heating having been long enough within the recited parameters so that the product upon fractionation is substantially free from anti-complement activity.

2. A method according to claim 1, wherein fractionation is effected with alcohol.

3. A method according to claim 1, wherein fractionation is effected with ammonium sulfate.

4. A method according to claim 1, wherein heating is effected for about 2 hours at about 56° C.

5. An intravenously applicable native human immune globulin produced by the process of claim 1.

* * * * *

| Specimen | ml of complement per ml of specimen | 2 | 4 | 6 | 8 | 10 | 12 | 14 | 16 | 18 |
|---|---|---|---|---|---|---|---|---|---|---|
| Plasma |  | ☨ ☨ | + | − | − | − | − | − | − | − |
| IgG I |  | ☨ ☨ ☨ ☨ | ☨ ☨ ☨ ☨ | − | − | − | − | − | − | ☨ ☨ ☨ ☨ |
| IgG II |  | ☨ ☨ ☨ ☨ | ☨ ☨ | +− | − | − | − | − | − | − |

Key: - Total hemolysis: no anti-complement activity
☨ ☨ ☨ ☨ : No hemolysis: anti-complement activity
☨ ☨ : 50% hemolysis
IgG I : Cohn fraction II from native plasma (purity over 95%)
IgG II: Cohn fraction II from heated plasma (purity over 95% immune globulin G).